US008685058B2

(12) United States Patent
Wilk

(10) Patent No.: US 8,685,058 B2
(45) Date of Patent: Apr. 1, 2014

(54) SURGICAL CLOSURE METHOD AND ASSOCIATED DEVICE

(75) Inventor: Peter J. Wilk, New York, NY (US)

(73) Assignee: Wilk Patent, LLC, New York, NY (US)

( * ) Notice: Subject to any disclaimer, the term of this patent is extended or adjusted under 35 U.S.C. 154(b) by 2331 days.

(21) Appl. No.: 11/369,477

(22) Filed: Mar. 7, 2006

(65) Prior Publication Data

US 2006/0217745 A1 Sep. 28, 2006

Related U.S. Application Data

(60) Provisional application No. 60/664,435, filed on Mar. 23, 2005.

(51) Int. Cl.
*A61D 1/00* (2006.01)

(52) U.S. Cl.
USPC ............................ 606/213; 606/142; 606/219

(58) Field of Classification Search
USPC ......... 606/139, 142–144, 148, 149, 213, 215, 606/216, 219, 221
See application file for complete search history.

(56) References Cited

U.S. PATENT DOCUMENTS

| | | | |
|---|---|---|---|
| 4,006,747 A * | 2/1977 | Kronenthal et al. | .......... 606/144 |
| 4,506,669 A | 3/1985 | Blake, III | |
| 5,236,440 A * | 8/1993 | Hlavacek | ..................... 606/219 |
| 5,297,536 A | 3/1994 | Wilk | |
| 5,458,131 A | 10/1995 | Wilk | |
| 5,944,715 A | 8/1999 | Goble et al. | |
| 5,964,782 A | 10/1999 | Lafontaine et al. | |
| 6,068,638 A | 5/2000 | Makower | |
| 6,547,821 B1 | 4/2003 | Taylor et al. | |
| 6,746,460 B2 * | 6/2004 | Gannoe et al. | ................. 606/153 |
| 2003/0236535 A1* | 12/2003 | Onuki et al. | .................. 606/144 |
| 2004/0215216 A1 | 10/2004 | Gannoe et al. | |
| 2004/0225183 A1 | 11/2004 | Mitchlitsch et al. | |
| 2005/0203489 A1 | 9/2005 | Saadat et al. | |
| 2005/0216040 A1 | 9/2005 | Gernter et al. | |
| 2005/0247320 A1 | 11/2005 | Stack et al. | |

FOREIGN PATENT DOCUMENTS

WO          WO/99/62415        12/1999

OTHER PUBLICATIONS

Office Action from U.S. Appl. No. 11/369,618, filed Mar. 7, 2006.
Office Actions (2) from U.S. Appl. No. 11/369,618, filed Mar. 7, 2006.

* cited by examiner

*Primary Examiner* — Dianne Dornbusch
(74) *Attorney, Agent, or Firm* — R. Neil Sudol; Henry D. Coleman

(57) ABSTRACT

In a surgical method, an incision is formed in a layer of organic tissue defining a wall having an inner side and an outer side. The incision has a pair of opposing lips or edges. The lips or edges are retracted towards the inner side of the tissue wall and approximated to one another. Thereafter, one or more closure elements are applied to the inwardly pulled lips or edges.

8 Claims, 5 Drawing Sheets

SURGICAL CLOSURE METHOD AND ASSOCIATED DEVICE

CROSS-REFERENCE TO RELATED APPLICATION

This application claims the benefit of U.S. Provisional Patent Application No. 60/664,435 filed Mar. 23, 2005.

BACKGROUND OF THE INVENTION

This invention relates to a surgical closure method. The method of the invention is particularly useful in medical surgical procedures carried out without the formation of an incision in a skin surface of the patient.

Such procedures are described in U.S. Pat. Nos. 5,297,536 and 5,458,131.

As described in those patents, a method for use in intra-abdominal surgery comprises the steps of (a) inserting an incising instrument with an elongate shaft through a natural body opening into a natural body cavity of a patient, (b) manipulating the incising instrument from outside the patient to form a perforation in an internal wall of the natural internal body cavity, and (c) inserting a distal end of an elongate surgical instrument through the natural body opening, the natural body cavity and the perforation into an abdominal cavity of the patient upon formation of the perforation. Further steps of the method include (d) inserting a distal end of an endoscope into the abdominal cavity, (e) operating the surgical instrument to perform a surgical operation on an organ in the abdominal cavity, (f) viewing the surgical operation via the endoscope, (g) withdrawing the surgical instrument and the endoscope from the abdominal cavity upon completion of the surgical operation, and (h) closing the perforation.

Visual feedback may be obtained as to position of a distal end of the incising instrument prior to the manipulating thereof to form the perforation. That visual feedback may be obtained via the endoscope or, alternatively, via radiographic or X-ray equipment.

The abdominal cavity may be insufflated prior to the insertion of the distal end of the endoscope into the abdominal cavity. Insufflation may be implemented via a Veress needle inserted through the abdominal wall or through another perforation in the internal wall of the natural body cavity. That other perforation is formed by the Veress needle itself. U.S. Pat. No. 5,209,721 discloses a Veress needle that utilizes ultrasound to detect the presence of an organ along an inner surface of the abdominal wall.

A method in accordance with the disclosures of U.S. Pat. Nos. 5,297,536 and 5,458,131 comprises the steps of (i) inserting an endoscope through a natural body opening into a natural body cavity of a patient, (ii) inserting an endoscopic type incising instrument through the natural body opening into the natural body cavity, (iii) manipulating the incising instrument from outside the patient to form a perforation in an internal wall of the natural internal body cavity, (iv) moving a distal end of the endoscope through the perforation, (v) using the endoscope to visually inspect internal body tissues in an abdominal cavity of the patient, (vi) inserting a distal end of an elongate surgical instrument into the abdominal cavity of the patient, (vii) executing a surgical operation on the internal body tissues by manipulating the surgical instrument from outside the patient, (viii) upon completion of the surgical operation, withdrawing the surgical instrument and the endoscope from the abdominal cavity, (ix) closing the perforation, and (x) withdrawing the endoscope from the natural body cavity.

The surgical procedures of U.S. Pat. Nos. 5,297,536 and 5,458,131 reduces trauma to the individual even more than laparoscopic procedures. Hospital convalescence stays are even shorter. There are some potential problems with the procedures, such as the difficulty in forming a fluid tight closure of the perforation formed in the wall of the hollow internal body organ. Certain intra-abdominal operations cannot be easily performed owing to the necessity or removing large chunks of organic or inorganic material (e.g., entire kidney, gall stones). Some operations can require the simultaneous usage of many different instruments so that space along the selected pathways may be difficult to find.

The above-described procedures may be described generally as trans-organ surgical procedures, whereby a surgical operation performed on one organ is effectuated through the wall of another organ, which is at least partially hollow. Preferably such a procedure is conducted via a natural body opening communicating with the hollow organ, as described in the above cited prior patents of applicant.

Such a trans-organ procedure typically, but not necessarily, requires the closure of an incision formed in the wall of the hollow organ. Where the organ has a mucosal layer along one surface (generally on the side communicating with the natural body opening), problems may arise owing to the natural difficulty that joined mucosal tissues have in healing.

OBJECTS OF THE INVENTION

It is an object of the present invention to provide a surgical closure method.

A more particular object of the present invention is to provide a surgical closure method utilizable in the afore-described surgical procedures.

A further object of the present invention is to provide a surgical closure method that is effective in closing incisions or wounds in mucosal tissues.

A related object of the present invention is to provide an associated device for use in the method.

These and other objects of the present invention will be apparent from the drawings and detailed descriptions herein. While every object of the invention is believed to be attained in at least one embodiment of the invention, there is not necessarily any single embodiment that achieves all of the objects of the invention.

SUMMARY OF THE INVENTION

A surgical method comprises, in accordance with the present invention, forming an incision in a layer of organic tissue defining a wall having an inner side and an outer side. The incision has a pair of opposing lips or edges. The lips or edges are pulled towards the inner side of the tissue wall. Thereafter, at least one closure element is applied to the inwardly pulled lips or edges.

Typically, the inner side of the wall has a layer of mucosal tissues, while the outer side has a tissue composition that more easily fuses or joins to itself during a healing process. The present invention thus aims to ensure that the tissues on the outer side of the wall are placed in contact with one another when the incision is closed and clamped.

In one embodiment of the present invention, the pulling of the lips or edges towards the inner side of the tissue wall includes inserting a distal end of an approximating or retracting tool through the incision from the inner side to the outer side of the wall. The distal end is provided with a plurality of barbs. The tool is manipulated to insert the barbs into the wall on opposite sides of the incision on the outer side of the wall.

Thus, the incision lips or edges are hooked on the outer side of the wall and drawn inwardly, in the direction from the outer side to the inner side of the wall.

The barbs are preferably removed from the wall after the applying of the closure element. The distal end of the tool is then withdrawn through the incision, that is, back towards the inner side from the outer side.

Where the tool has a distal shaft portion extending along a tool axis, the barbs are preferably located in a plane including the axis. The manipulating of the tool to insert the barbs into the wall then includes rotating the shaft so that the plane is oriented at an angle relative to the incision. Accordingly, the invention contemplates that prior to moving the distal end of the tool through the incision, the tool is rotated so that the plane of the barbs lies parallel to and coincident with the plane of the incision (in the case of a slit-type incision or wound).

The invention further contemplates that multiple closure elements may be applied to the inwardly pulled lips or edges of the incision. A plurality of such closure elements may be applied prior to the disengagement and withdrawal of the distal end of the tool from the region of the incision. In addition, at least one closure element should be applied to the incision after the distal end of the tool has been withdrawn. This is to seal the incision or wound at the point of placement or engagement of the tool with the incision lips or edges.

The closure elements may be sutures. In a trans-organ procedure as described in U.S. Pat. Nos. 5,297,536 and 5,458,131, sutures may be applied with an elongate flexible suturing technique as described in U.S. Pat. No. 5,037,433.

The closure elements may be staples or clips. In a trans-organ procedure as described in U.S. Pat. Nos. 5,297,536 and 5,458,131, staples may be applied with an elongate flexible stapling technique as described in U.S. Pat. Nos. 5,015,249, 5,049,153, and 5,156,609. The staples or clips may have a form described and illustrated in U.S. Pat. No. 5,222,961.

The closure elements alternatively may take the form of tacks.

In an alternative embodiment of the present invention, the pulling of the incision lips or edges includes attaching a surgical device to the wall on the inner side thereof so that the device engages both the lips or edges, and drawing the device inwardly away from the wall. The device may be a clip that is removably attached to the incision lips or edges. Alternatively and more efficiently, the clip is left in place as a closure element securing the incision. The drawing of the device includes pulling a tensile element such as a string connected to the clip. Where the clip is left in place as a closure element, the string may be cut after the other closure elements have been attached to the drawn incision lips.

Where only one clip is used as a pulling device, the clip is preferably attached at a central location along the incision. Where more than one clip are applied as pulling elements, the clips are attached to the wall at spaced positions along the incision.

In a trans-organ surgical procedure as described in U.S. Pat. Nos. 5,297,536 and 5,458,131, the pulling of the incision lips or edges towards the inner side and the applying of the closure element(s) to the inwardly pulled lips or edges both include manipulating instruments inserted into the patient through a natural body opening such as a mouth or a nostril, a vaginal opening, a urethral opening or a rectal orifice. The present method may be used to close an incision made in the wall of an organ communicating with the natural body opening. Such an organ may be the stomach, the vagina, the urinary bladder or the colon. Alternatively or additionally, the present method may be used to close an incision made in another organ, for example, in the abdominal cavity of the patient, which does not communicate with the ambient environment via a natural body opening. Thus, an incision made in the abdominal wall of the patient, for example, for the insertion of a laparscope or other surgical instruments, may be closed from inside the abdomen via elongate flexible closure instruments inserted into the abdominal cavity via the stomach, the vagina, the urinary bladder or the colon.

The method of the present invention may be used in surgical procedures other than the trans-organ procedures described in U.S. Pat. Nos. 5,297,536 and 5,458,131. For instance, in a laparoscopic procedure having multiple incisions formed in the abdominal wall, all but one of the incisions may be as described herein, where the approximating or retracting tool, a flexible laparoscope, and the closure clips are inserted into the abdominal cavity via the same trans-abdominal incision. In another example, the method of the invention, including the pulling of the lips or edges towards the inner side and the applying of the closure element to the inwardly pulled lips or edges, may be effectuated via a blood vessel, especially a vein.

The method of the present invention is particularly useful in trans-organ surgical operations as described in U.S. Pat. Nos. 5,297,536 and 5,458,131. Accordingly, a surgical instrument is inserted through the incision prior to the pulling (retracting and approximately) of the incision lips or edges. The surgical instrument is manipulated to perform a surgical operation on internal body tissues of the patient on the outer side of the wall.

A surgical instrument utilizable in a method in accordance with the present invention comprises an elongate flexible shaft and a plurality of barbs provided on a distal end of the shaft, the shaft extending along a tool axis at the distal end of the shaft, the barbs being located in a plane including the axis.

Another surgical tool in accordance with the present invention comprises a pair of clip or staple jaws and an elongate tensile element connected to the jaws at a hinged end thereof.

A surgical instrument kit comprises, in accordance with the present invention, an instrument for forming an incision in a layer of organic tissue defining a wall having an inner side and an outer side, the incision having a pair of opposing lips or edges, a tool engageable with the organ wall and utilizable to pull the lips or edges towards the inner side, and at least one closure element for coupling to the inwardly pulled lips or edges to maintain the lips approximated to one another.

In one embodiment of a kit, the tool has a distal end provided with a plurality of barbs, the tool being manipulatable to insert the barbs into the organ wall on opposite sides of the incision on the outer side of the organ wall. This tool may have a shaft extending along a tool axis, with the barbs all being located in a plane including the axis, so that the tool may be rotated so that the plane is oriented at a controllable angle relative to the incision.

Alternatively, the tool may be a surgical device attachable to the organ wall on the inner side thereof so that the tool engages both of the lips or edges and may be drawn to drag the lips or edges inwardly away from the organ wall. The surgical device may be a clip with a flexible tensile element connected thereto.

The closure element is taken from the group consisting of a staple, a clip, a suture, and a tack.

DETAILED DESCRIPTION

Figure 1:
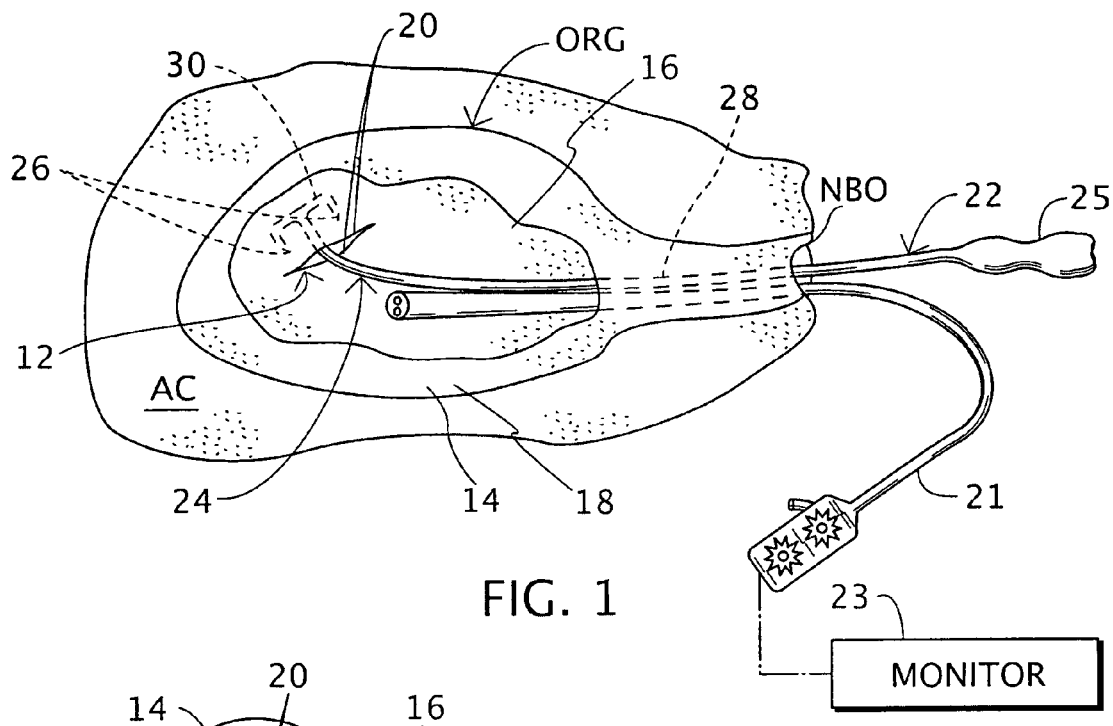
FIG. 1 is a schematic view of a hollow human organ, partially broken away, to show a step in a trans-organ surgical closure operation in accordance with the present invention.

FIG. 1 shows a hollow organ ORG that communicates with the ambient environment via a natural body opening NBO. During a trans-organ surgical procedure as described in U.S. Pat. Nos. 5,297,536 and 5,458,131 (both incorporated by reference herein), an incision 12 is formed in a wall 14 of organ ORG by means of instruments (not shown) inserted into organ ORG via natural body opening NBO. Natural body opening NBO may be the mouth, a nostril, the vaginal orifice, the anus, or the urethral opening. Concomitantly, organ ORG may be the stomach, the vagina, the colon, or the urinary bladder. All of these organs are located in the abdominal cavity AC and thus form an avenue of access to other abdominal organs pursuant to the procedures described in U.S. Pat. Nos. 5,297,536 and 5,458,131.

Wall 14 of organ ORG is one or more layers of organic tissue having an inner side 16 and an outer side 18 (FIGS. 2A-2D). Incision 12 has a pair of opposing lips or edges 20. Where incision 12 has a circular configuration as in a puncture wound, lips or edges 20 are opposing portions along the rim of the puncture wound.

FIG. 1 shows an endoscope 21 inserted into organ ORG through natural body opening NBO. The endoscope may be used to produce images on a monitor 23 to enable surgical personnel to visualize a surgical closure operation as described herein with reference to FIGS. 1 and 2A-2E, as well as FIGS. 3A, 3B, and 4.

Figure 2A:
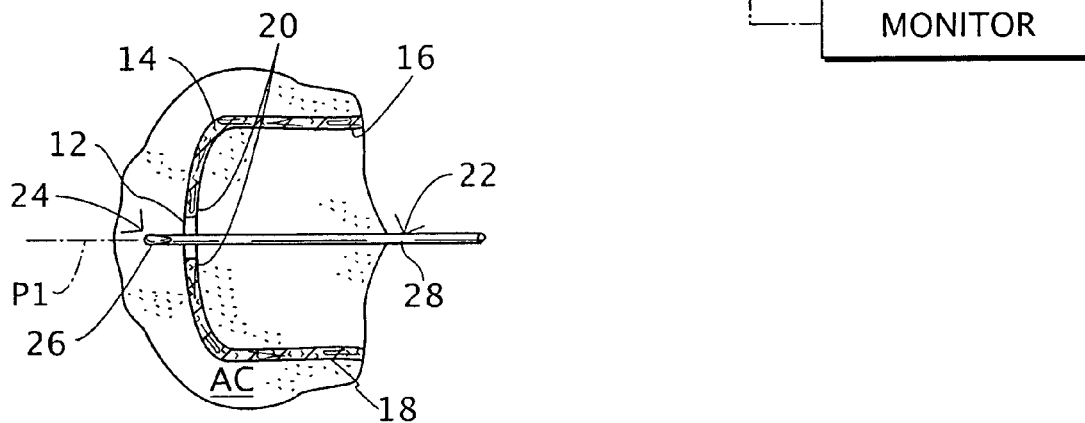
FIGS. 2A-2D are schematic cross-sectional views of the organ of FIG. 1, showing successive steps in the incision closure operation in accordance with the present invention.
Figure 2B:
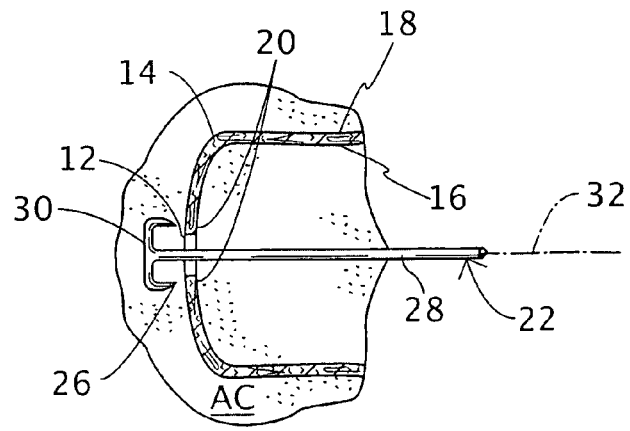

As shown in FIGS. 1 and 2B, closure of incision 12 (after the performance of an intra-abdominal operation) includes the insertion of a retracting and approximating tool 22 having a handgrip 25 at a proximal end and a distal end portion 24 formed with a pair of barbs 26 that point back along a shaft 28 of tool 22. FIGS. 1 and 2B show barbs 26 as located at opposite ends of a crossbar 30 oriented generally perpendicularly to shaft 28 at distal end portion 24. Preferably, crossbar 30 is short to ensure that barbs 26 are proximate to one another for purposes of facilitating an approximation of lips or edges 20 as described below. Barbs 26 may extend in the manner of fishing hooks directly from shaft 28, thus eliminating crossbar 30.

Figure 2C:
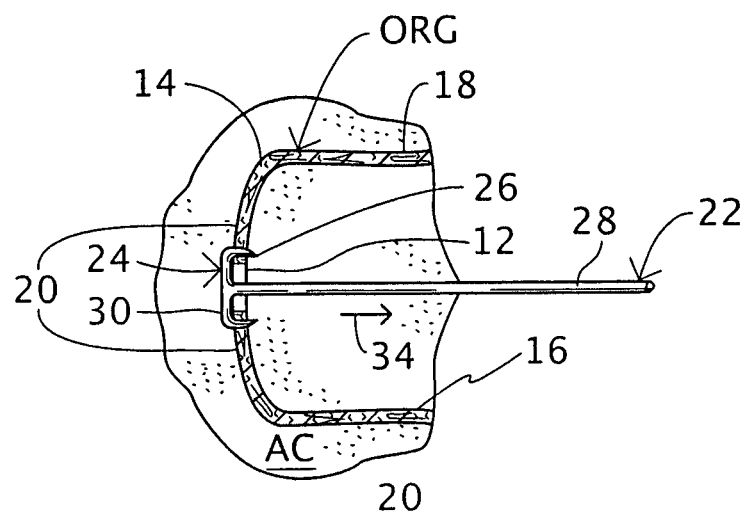
Figure 2D:
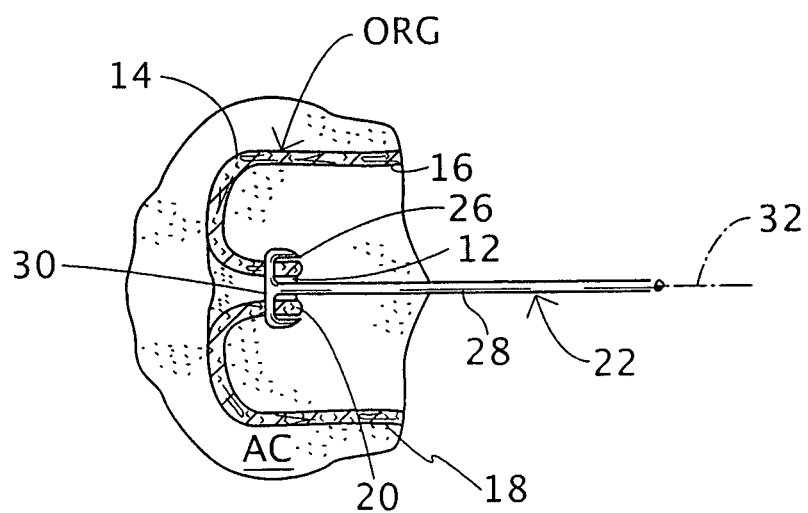
Figure 2E:
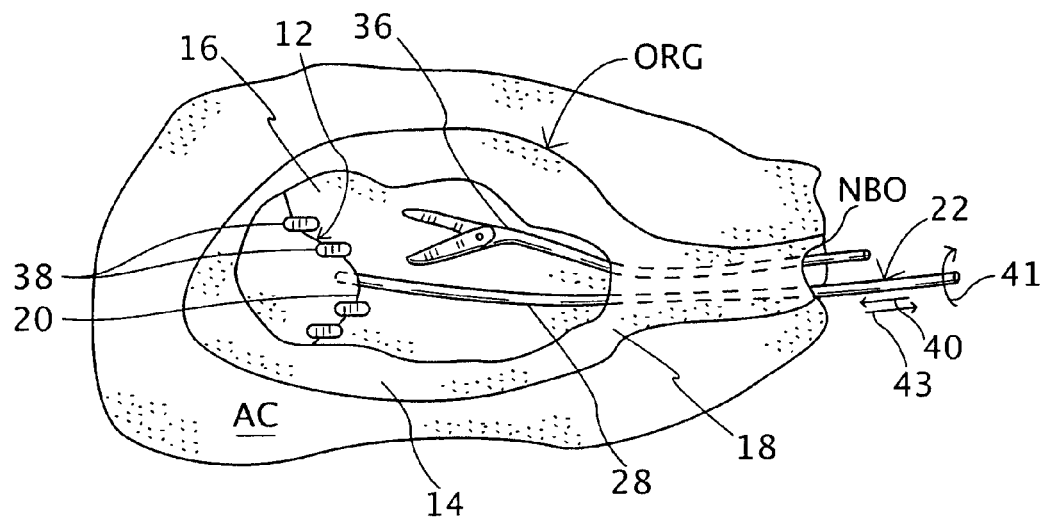
FIG. 2E is a schematic view of the organ of FIGS. 1 and 2A-2D, showing another step in the incision closure operation.

Barbs 26 and crossbar 30 are located in a plane P1 (FIG. 2A) including an axis 32 of shaft 28 at distal end portion 24. Upon a disposition of distal tool portion 24 in organ ORG, tool 22 is manipulated from outside the patient to orient crossbar 30 and barbs 26 so that they may be inserted through incision 12. A rotation of tool shaft 28 about axis 32 turns plane P1 into alignment with incision 12, as indicated in FIG. 2A. Tool shaft 28 is then pushed further into the patient, in the distal direction, so that barbs 26 and crossbar 30 are located in the abdominal cavity AC. Thereafter tool shaft 28 is rotated from outside the patient so that the plane P1 formed by crossbar 30 and barbs 26 is oriented at an angle to incision 12, as illustrated in FIG. 2B. Subsequently, tool 22 is pulled in the proximal direction, as indicated by an arrow 34 in FIG. 2C, so that barbs 26 penetrate through outer organ surface 18 into organ wall 14 on opposite sides of incision 12, i.e., into lips or edges 20 (FIG. 2C). Further motion of tool shaft 28 in the proximal direction pulls lips or edges 20 into organ ORG (in the direction of inner side 16) so that the outer wall surfaces of incision lips or edges 20 are approximated to one another, as illustrated in FIG. 2D. Instrumentation such as a clip applier 36 is then inserted into organ ORG via natural body opening NBO, as depicted in FIG. 2E, for purposes of placing a series of closure elements 38 along the approximated lips or edges 20. The closure elements 38 so placed are spaced sufficiently from tool shaft 28 to allow a removal of barbs 26 and crossbar 30 from abdominal cavity AC through incision 12. In that procedure, tool 22 is pushed in the distal direction, as indicated by an arrow 40 in FIG. 2E, to disengage barbs 26 from organ wall 14. A rotation (arrow 41) of shaft 28 is necessary to bring plane P1 in alignment with the partially closed incision 12 so that the tool head (26, 30) may be brought into organ ORG via incision 12 and subsequently out of the organ through natural body opening NBO (arrow 43). After the tool head is pulled through the partially closed incision 12, one or more additional closure elements 38 are applied to the incision complete the closure operation.

Typically, inner side 16 of organ wall 14 has a layer of mucosal tissues, while outer side 18 has a tissue composition that more easily fuses or joins to itself during a healing process. The procedure described above serves to ensure that the tissues on the outer side 18 of wall 14 are disposed in contact with one another when incision 12 is closed, thereby facilitating the healing process.

Closure elements 38 may take the form of sutures. In the procedure described above, sutures may be applied with an elongate flexible suturing technique as described in U.S. Pat. No. 5,037,433.

Alternatively, closure elements 38 may take the form of staples or clips. In the procedure described above, staples may be applied with an elongate flexible stapling technique as described in U.S. Pat. Nos. 5,015,249, 5,049,153, and 5,156, 609. The staples or clips may have a form described and illustrated in U.S. Pat. No. 5,222,961.

Alternatively, closure elements 38 may take the form of tacks.

Figure 3A:
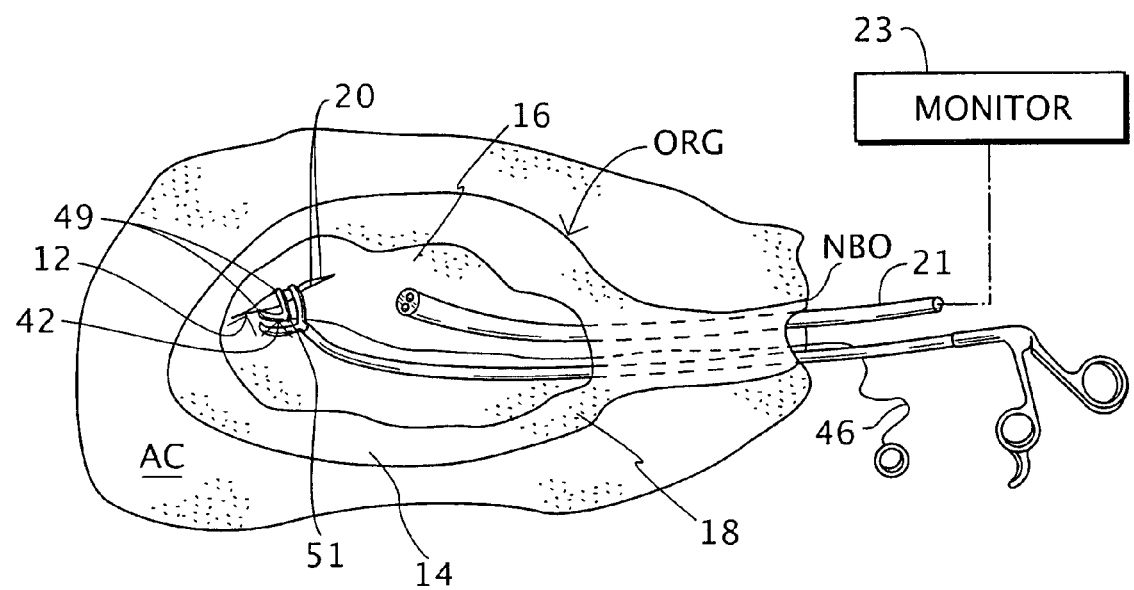
FIGS. 3A and 3B are views respectively similar to FIGS. 1 and 2E, showing steps in an alternative incision closure operation in a trans-organ surgical procedure, in accordance with the present invention.
Figure 3B:
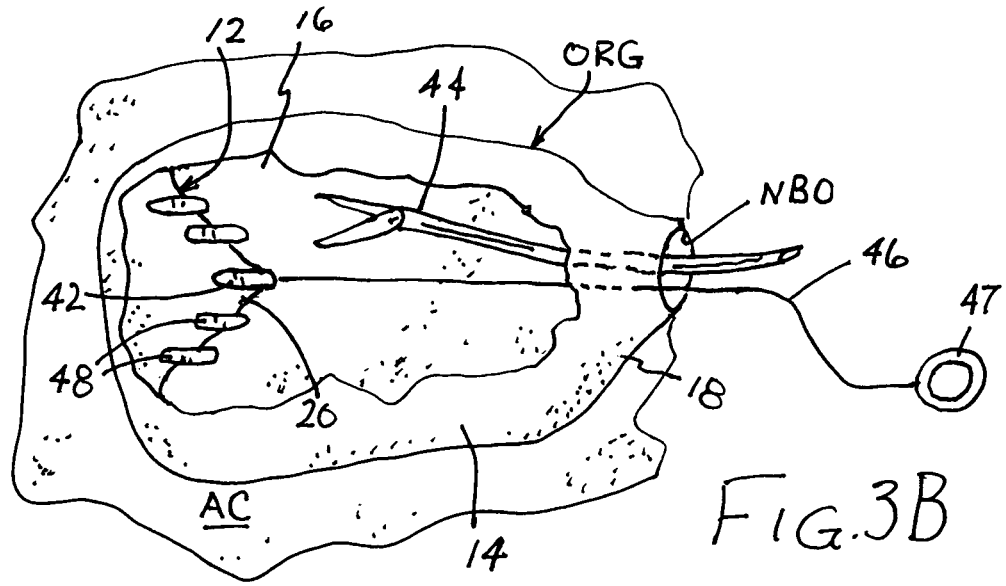

In an alternative closure method illustrated in FIGS. 3A and 3B, incision lips or edges 20 are pulled towards the inner side of wall 14, into organ ORG, by attaching a surgical device 42 to the organ wall on the inner side 16 thereof so that the device engages both lips or edges 20 and by drawing the device inwardly away from wall 14. As depicted in FIG. 3A, surgical device 42 is a clip or staple that is applied to organ wall 14 along opposing incision lips or edges 20 by a clip applier 44 partially inserted into organ ORG via natural body opening NBO. Preferably, clip or staple 42 is left in place as a closure element securing incision 12.

As discussed above with respect to the embodiments of FIGS. 1 and 2A-2E, clip or staple 42 with lips or edges 20 entrained thereto is drawn into organ ORG to approximate the outer surfaces of the incision lips or edges prior to closure of the incision, to facilitate the eventual healing of the tissues at the incision 12. Clip or staple 42 is drawn into organ ORG by pulling a tensile element 46 such as a string connected to the clip or staple at one end and to a pull ring 47 at an opposite end. Where clip or staple 42 is left in place as a closure element, string 46 may be cut after other closure elements 48 have been attached to the drawn incision lips 20 by clip applier 44 (FIG. 3B).

Figure 4:
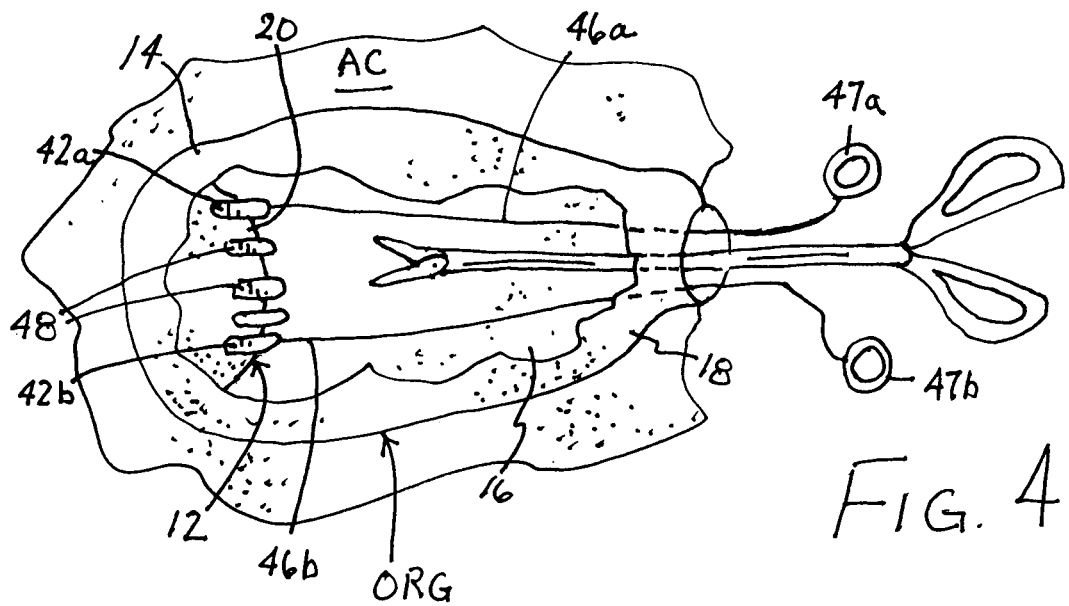
FIG. 4 is a view similar to FIG. 3B, showing a modification of the incision closure operation of FIGS. 3A and 3B.

Clip or staple 42 has a pair of jaws 49 pivotably connected to one another at a hinge or joint 51. String 46 is connected to clip 42 at hinge or joint 51.

Where only one clip 42 is used as a pulling device, the clip is preferably attached at a central location along the incision as depicted in FIGS. 3A and 3B. Where more than one clip 42a and 42b are applied as pulling elements, as depicted in FIG. 4, the clips are attached to the organ wall 14 at spaced positions along the incision 12. Clips 42a and 42b are secured to ends of strings 46a, 46b in turn coupled at opposite ends to pull rings 47a, 47b.

In a trans-organ surgical procedure as described hereinabove, the pulling of the incision lips or edges 20 towards the inner side 16 and the applying of the closure element(s) 38 or 42, 42a, 42b, 48 to the inwardly pulled lips or edges include manipulating instruments inserted into the patient through natural body opening NBO, which may be a mouth or a nostril, a vaginal opening, a urethral opening or a rectal orifice. The method as described in detail above is used to close incision 12, that incision having been made in wall 14 of organ ORG, that organ communicating with the natural body opening NBO. Such an organ ORG may be the stomach, the vagina, the urinary bladder or the colon. Alternatively or additionally, the same technique may be used to close an incision made in another organ, for example, in the abdominal cavity AC of the patient, which does not communicate with the ambient environment via a natural body opening. Thus, an incision 50 (FIG. 5) made in the abdominal wall AW of the patient, for example, for the insertion of a laparscope or other surgical instruments (none shown), may be closed from inside the abdominal cavity AC via elongate flexible closure instruments 52 inserted into the abdominal cavity via hollow organ ORG and natural body opening NBO. (Same reference labels designate same objects as in above description.)

Figure 5:
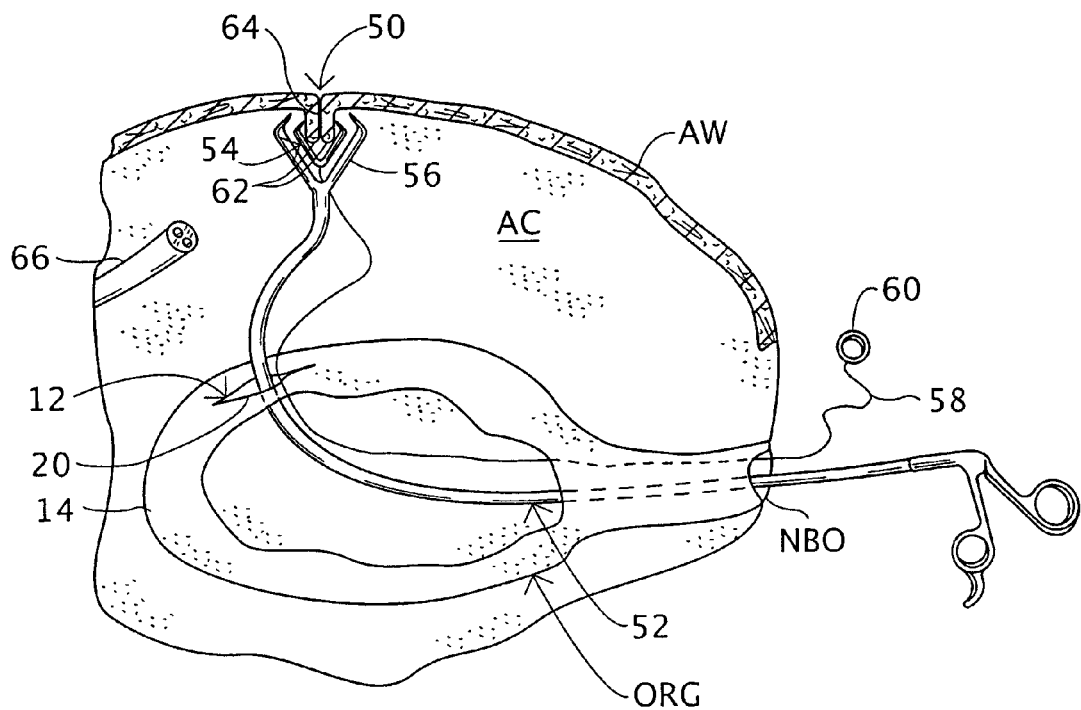
FIG. 5 is a schematic view, partially broken away, of a human abdominal cavity, showing a step in a surgical closure operation implemented via a natural body opening and a hollow organ, in accordance with the present invention.

Instrument 52 (FIG. 5) is a clip applier that is manipulated from outside the patient to deploy a pulling device 54 such as a staple or clip into abdominal wall AW from the inner side thereof. Instrument 52 has an operative head 56 with jaws (not separately designated), which is inserted into the patient through natural body opening NBO, organ ORG, incision 12, and abdominal cavity AC. Pulling device 54 is attached to a string 58 that extends from the pulling device back out through incision 12, organ ORG, and natural body opening NBO to a pull ring 60. Pulling on ring 60 places string 58 in tension to draw opposing lips or edges 62 of incision 50 into abdominal cavity AC so that outer skin surfaces 64 of the lips or edges are approximated and held for the placement of other closure elements (not separately shown) along the incision 50. FIG. 5 shows an endoscope 66 in abdominal cavity, which enables a visualization of the surgical closure operation.

Figure 6:
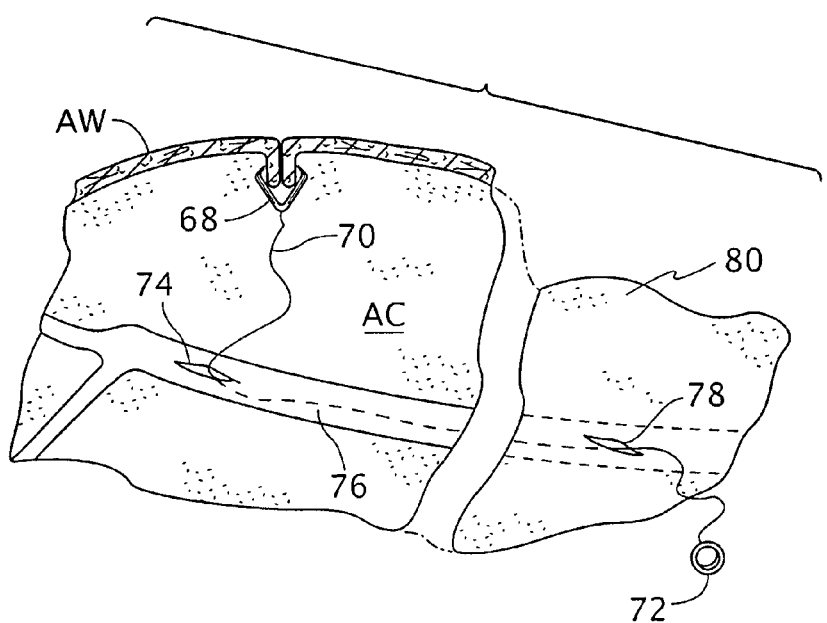
FIG. 6 is a schematic view, partially broken away, of a human abdominal cavity, showing a step in a surgical closure operation implemented via a patient's vascular system, in accordance with the present invention.

The method of the present invention may be used in surgical procedures other than the trans-organ procedures described in U.S. Pat. Nos. 5,297,536 and 5,458,131. For instance, as illustrated in FIG. 6, incision 50 in abdominal wall AW may be drawn into the abdominal cavity AC by a pulling clip 68 attached to a string 70 that extends out of the body to a pulling ring 72 via an incision 74 in a blood vessel 76 and an incision 78 in a skin surface 80. The incision closure procedures are essentially the same as described above, with access being obtained percutaneously through the patient's vascular system. Visualization may be obtained through an endoscope (not shown) inserted through a hollow organ such as the stomach, vagina, etc, or laparoscopically.

The surgical tools, instruments and closure elements described hereinabove may be provided in various combinations as kits for facilitating not only the distribution of the surgical tools, instruments and closure elements but also the deployment and utilization of the surgical tools, instruments and closure elements in the operating room.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical method comprising:
   forming an incision in a layer of organic tissue defining a wall of an organ, said wall separating an inner side of said organ from an outer side of said organ, said incision having a pair of opposing lips or edges;
   applying at least one first closure element to said lips or edges on said inner side of said wall, said at least one first closure element having jaws connected by a hinge or joint, a tensile element being connected to said at least one first closure element at said hinge or joint, the applying of said at least one first closure element including placing said jaws in contact with said lips or edges on said inner side of said wall;
   thereafter drawing said at least one first closure element towards said inner side of said wall to approximate said lips or edges to one another on said inner side of said wall and close said incision, the drawing of said at least one first closure element including pulling on said tensile element;
   after the drawing of said at least one first closure element towards said inner side of said wall and approximating said lips or edges to one another, applying at least one second closure element to said lips or edges on said inner said of said wall;
   maintaining tension on said tensile element during the applying of said at least one second closure element; and
   retaining said at least one first closure element attached to said wall on said inner side of said organ to maintain said incision in a closed state.

2. The method defined in claim 1 wherein the applying of said at least one first closure element including attaching said at least one first closure element at a central location along said incision.

3. The method defined in claim 1 wherein said at least one first closure element and said at least one second closure element are clips, the applying of said at least one first closure element and said at least one second closure element to said lips or edges including attaching said clips to said wall at spaced positions along said incision.

4. The method defined in claim 1 wherein the applying of said at least one first closure element and the drawing of said at least one first closure element both include manipulating members inserted into the patient through a natural body opening.

5. The method defined in claim 1 wherein the applying of said at least one first closure element and the drawing of said at least one first closure element both include manipulating members inserted into the patient through a blood vessel.

6. The method defined in claim 1, further comprising:
   insering a surgical instrument through said incision prior to the drawing of said at least one first closure element; and
   manipulating said surgical instrument to perform a surgical operation on internal body tissues of the patient on said outer side of said wall.

7. The method defined in claim 1 wherein said at least one first closure element is one of two first closure elements, the applying of said at least one first closure element including attaching said two first closure elements at spaced locations each proximate a respective end of said incision, a pair of tensile elements being provided each connected to a respective one of said first closure elements, further comprising pulling on said tensile elements after the attaching thereof and maintaining tension on said tensile elements during the applying of said at least one second closure element.

8. A surgical method comprising:
   forming an incision in a layer of organic tissue defining a wall having an inner side and an outer side, said incision having a pair of opposing lips or edges;
   inserting a distal end of a tool through said incision from said inner side to said outer side;
   manipulating said tool to pull said lips or edges towards said inner side; thereafter applying at least one closure element to said lips or edges on said inner side of said wall;
   subsequently withdrawing said distal end of said tool back through said incision; and
   thereafter applying at least one additional closure element to said lips or edges on said inner side of said wall.

\* \* \* \* \*